US006376221B1

(12) United States Patent
Fist et al.

(10) Patent No.: US 6,376,221 B1
(45) Date of Patent: Apr. 23, 2002

(54) PRODUCTION OF THEBAINE AND ORIPAVINE

(75) Inventors: Anthony John Fist, Norwood; Christopher James Byrne, Westbury; Wayne Lyle Gerlach, Killara, all of (AU)

(73) Assignee: Tasmanian Alkaloids Pty. Ltd., Westbury (AU)

( * ) Notice: Subject to any disclaimer, the term of this patent is extended or adjusted under 35 U.S.C. 154(b) by 0 days.

(21) Appl. No.: 09/387,374

(22) Filed: Aug. 31, 1999

Related U.S. Application Data

(62) Division of application No. 08/678,208, filed on Jul. 11, 1996, now Pat. No. 6,067,749.

(51) Int. Cl.$^7$ ............................................. C12P 17/16
(52) U.S. Cl. ..................... 435/118; 47/58.1; 424/725; 424/776; 514/289; 435/117; 435/119; 800/260; 800/295; 546/44; 546/45
(58) Field of Search ................................. 435/118, 117, 435/119; 424/725, 776; 514/289; 800/260, 295; 546/44.45

(56) References Cited

U.S. PATENT DOCUMENTS 6,067,749 A * 5/2000 Fist et al.

FOREIGN PATENT DOCUMENTS

WO        WO 98/02033        1/1998

OTHER PUBLICATIONS

Fairburn, J.W. and Helliwell, K., *Papaver bracteatun* Lindley: thebaine content in relation to plant development, I. Pharm. Pharmac., 1977, 29, pp. 65–69.
Seddich, Majid, Jolliff, Gary D.J. Calhoun, Wheller, and Crane, Jimmie M., *Papaver bracteatum*, Potential Commercial Source of Codeine, Econimic Botany, 36, 1982, pp. 433–441.
Duke, James A., Utilization of Papaver, Economic Botany, 27, 390–400, Oct.–Dec. 1974.
Fairburn, J.W., DSc, PhD, Sc, FPS, Dpharn., Phytoavailability and some of its problems, The Pharmaceutical Journal, Jan. 10, 1976, pp. 29–31.
Popov, P., Dimitrov, J., Georgiev, S. and Deneva, T., Radiosensitivity of Opium Poppy (*Papaver Somniferum I.*) and Morphine Content in the Dry Capsules of $M_1$ As Influenced by $CS^{137}$ Gamma Irradiation, Genetics and Plant Breeding, vol. 7, No. 4, pp. 251–257, 1974.
Karp, M.L., On the Occasional Absence of Opium in the Opium Poppy, Genetics, pp. 537–541.
Sudhair, Shukla and Khasma K.R., A Study of Gene Action for Opium Yield and Morphine Content in *Papaver Somniferum I.*, Indian J. Agric. Res. 29 (3), 116–120, 1995.

Pareek, S.K., Srivastava, V.K., Maheshwarj, M.L. and Gupta, R., Indian Journal of Agricultral Sciences 65 (7) pp. 498–502, Jul. 1995.
Shewry, P.R., Williamson, M.S. and Kreis, M., Effects of Mutant Genes on the Synthesis of Storage Components in Developing Barley Endosperms; pp. 94–119.
Caporale, Lynn Helena, Chemical ecology: A View From the pharmaceutical industry, Proc. Natl. Acad. Sci. USA, vol. 92, pp., 75–82, Jan. 1995.
Villalobos, Maria Jesus Pascual; Robbelen, Gerhard and Correal Enrique, Production and evaluation of indehiscent mutant genotypes in *Euphorbia lagascae*, Industrial Corps and Products 3 (1994) pp. 129–143.
Lea, P.J., Blackwell, R.D. and Azevedo, R.A., Analysis of Barley metabolism using Mutant Genes, pp. 181–209.
Lavanua, U.C. and Snvastiava, Sangeeta, Autotetraploid and triploid meiosis in *Papaver somniferum* show reduction in bound arm associations and enhanced bivalent pairing over generations, Current Research on Medicinal and Aromatic Plants, 17, (1995) pp. 10–13.
Thierfelder, A., Luhs, W., and Friedt, W., Breeding of industrial oil crops with the aid of biotechnology: a review; Industrial Crops and Products, 1 (1993) pp. 261–271.
Nyman, U., Selection for high thebaine/low morphine content in *Papaver somniferum L.*, Hereditas 93; pp. 121–124.
Singh, S.P., Shukla, Sudhir, Khanna, K.R., Diallel analysis for combining ability in opium poppy *Papaver somniferum*, Indian Journal of Agricultral Research, 65 (4) pp. 271–275.
Nyman, U., Poppy Seed—a crop that is coming back? Swedish Seed Association, issue 84; (1974).
Ben–Salah, H., Roath, W.W., Somaclonal variation in *Cuphea viscosissima Jacq.* For plant improvement, Industrial Crops and Products, 2, (1994) pp. 239–244.
Green, A.G., Genetic control of polyunsaturated fatty acid biosynthesis in flax (*Linum usitatissimum*) seed oil, Theor Appl Genet 72, (1986) pp. 654–661.
C.H., Opium– free poppy under study as a codeine source, Science 190 (1975) p. 1274.
Szymanowska, E., Liersch, J., Krzymanski, J. (Low Morphine poppy Przemko) *Mak niskomorfinowy Prezemko*, In Oilseed crops. XVIth Polish research conference, Apr. 19–20, 1994, Rosliny Oleiste, 15. (1) pp. 171–172.
Shukla Sudhir, Khanne, K.R. and S.P. Singh, Alkaloid Spectrum of Opium of a Cross Between Papaver Somniferum and P. Setigerum, International Journal of Pharmacognosy 1995, vol. 33, No. 3, pp. 228–231.

* cited by examiner

Primary Examiner—Leon B. Lankford, Jr.
(74) Attorney, Agent, or Firm—John Harbour (57) ABSTRACT

There is disclosed an improved poppy straw of a stably reproducing Papaver somniferum for the extraction of thebaine and/or oripavine, the threshed straw having thebaine and oripavine constituting about 50% by weight or greater of the alkaloid combination consisting of morphine, codeine, thebaine and oripavine.

10 Claims, 2 Drawing Sheets

FIG. 1

FIG. 2

PRODUCTION OF THEBAINE AND ORIPAVINE

Figure 1:
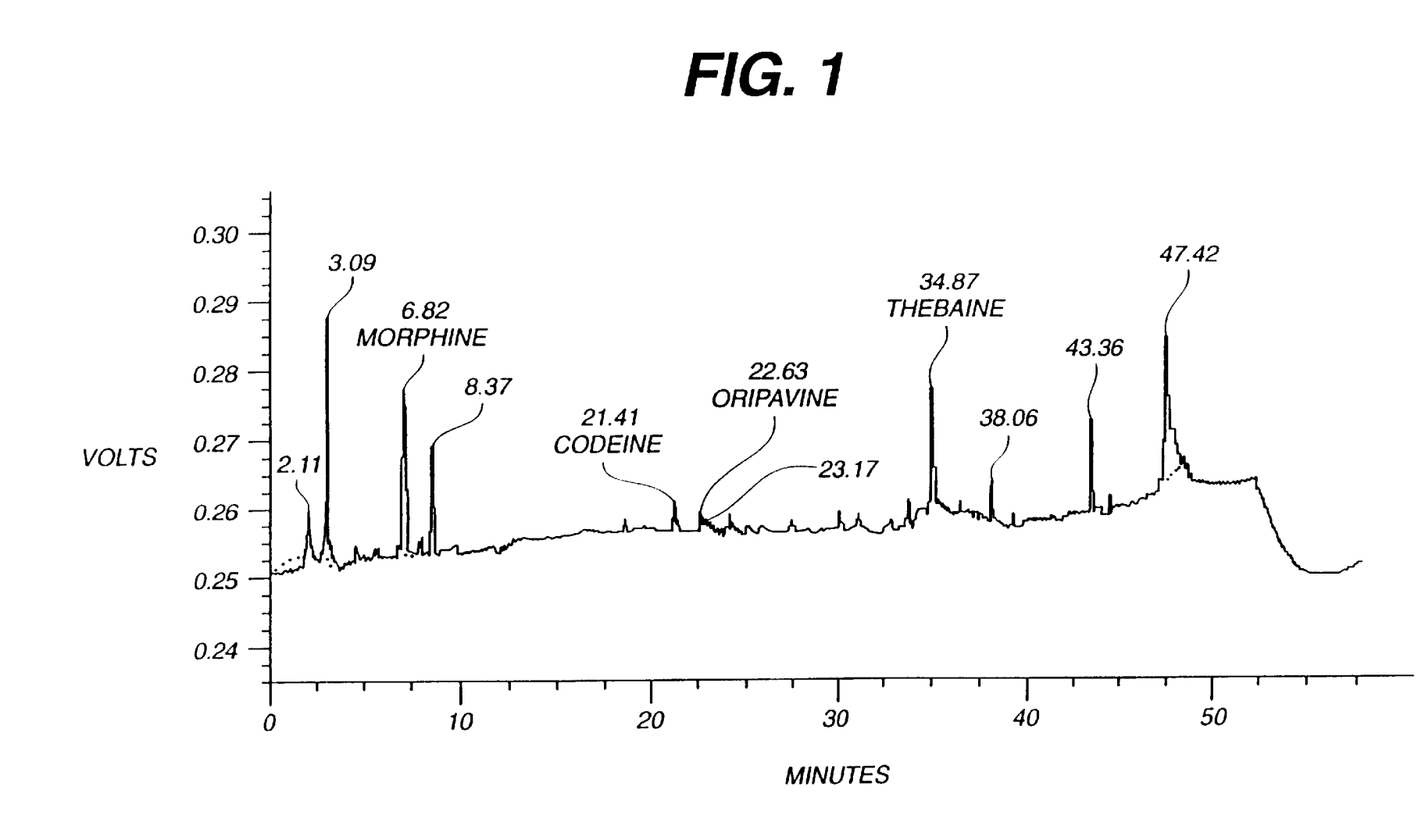
Figure 2:
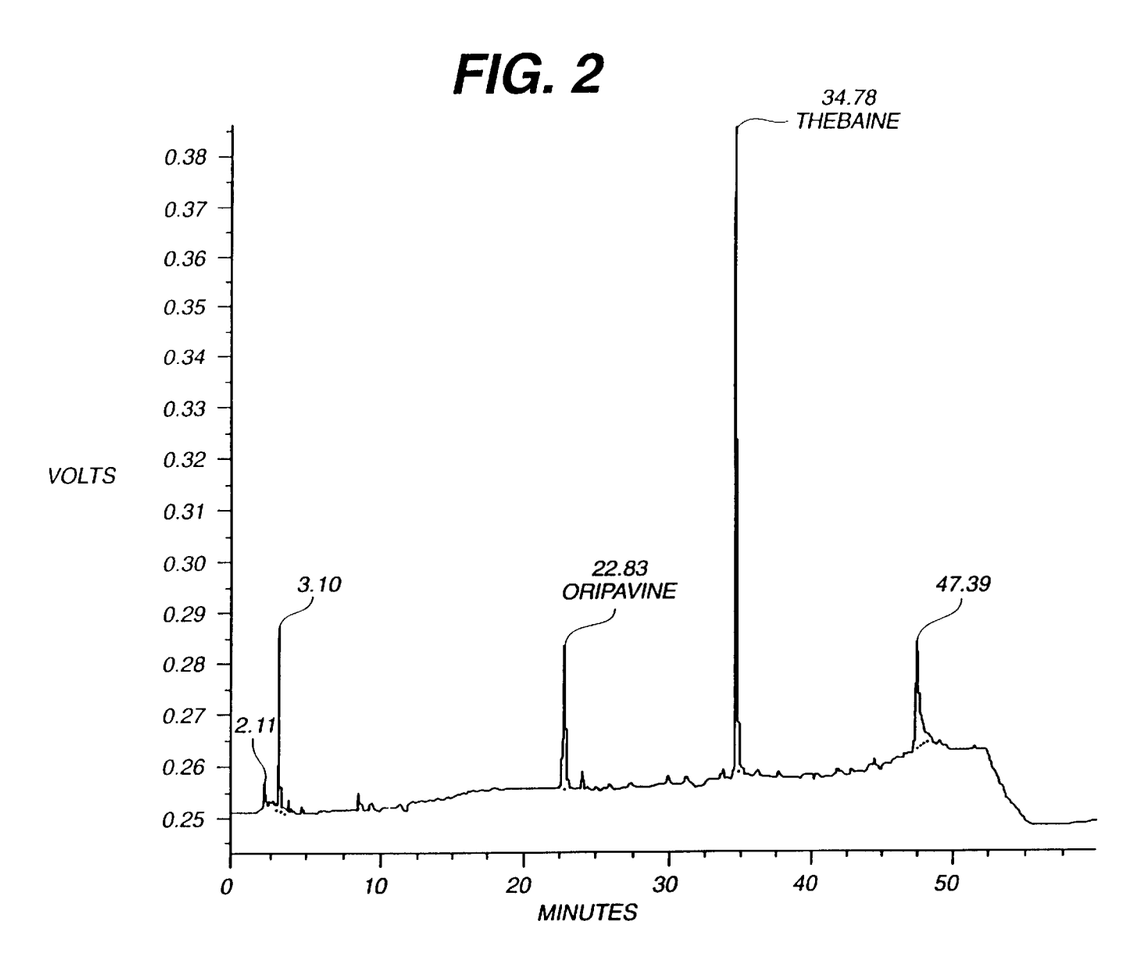

This is a divisional of prior application Ser. No. 08/678,208, filed Jul. 11, 1996, now U.S. Pat. No. 6,067,749.

The present invention relates to the improved production of thebaine and oripavine. More particularly, the present invention relates to the use of a mutagenized Papaver somniferum poppy plant to produce thebaine and oripavine in higher yield.

BACKGROUND OF THE INVENTION

The 14-hydroxymorphinans, such as, oxycodone, naloxone, naltrexone, nalbuphine and nalmefene are important opiate derivatives due to their behavior as potent analgesics and/or narcotic antagonists. The most practical synthetic routes to the preparation of these pharmaceuticals have utilized the alkaloid, thebaine, as a starting material. Other important opiate derivatives such as the ring-C bridged compounds buprenorphine and etorphine are also most practically prepared from thebaine.

Thebaine

In accordance with one conventional process, thebaine is oxidized to 14-hydroxycodeinone by use of m-chloroperbenzoic acid in an acetic acid/trifluoroacetic acid mixture or by a mixture of hydrogen peroxide and formic acid. 14-hydroxycodeinone is catalytically reduced to oxycodone. Oxycodone is a product sold for use as and analgesic and its production consumes large amounts of thebaine.

Oxycodone can be, in turn, O-demethylated with boron tribromide to yield oxymorphone. After blocking of the hydroxyl groups with a suitable blocking agent, such as, acetyl groups, the oxymorphone derivative is reacted with cyanogen bromide in a von Braun demethylation to yield an N-cyanodihydronormorphinone derivative that is thereafter hydrolyzed to 14-hydroxydihydronormorphinone (noroxymorphone). Noroxymorphone can be readily converted to nal-compounds by N-alkylation with appropriate alkyl halide, or acylation with appropriate acyl halide or anhydride, followed by reduction. A more generally applicable process, converts the oxycodone of the above process to noroxycodone by the von Braun N-demethylation followed by conversion to a 3-O-methyl-nal-compound using N-alkylation with an appropriate alkyl halide, or by alkylation with an appropriate alkyl halide, or acylation with appropriate acyl halide or anhydride, followed by reduction. The 3-O-methyl-nal-compound is reacted to a nal-compound by O-demethylation.

A synthesis using thebaine to produce the ring-C bridged opiate, buprenorphine, is shown in Scheme A1.

Flow Scheme A1

Another synthesis using thebaine to produce the 14-hydroxymorphinan, naltrexone as representative of the nal-compounds, is shown in Scheme A2.

Flow Scheme A2 thebaine oxycodone

3-O-methylnaltrexone naltrexone

Although these syntheses are effective, the availability of thebaine is limited and its cost high. The high cost of thebaine contributes to the high cost of the 14-hydroxymorphinans derived from it.

One reason for the limited availability of thebaine, and its high cost, is that total synthesis is difficult. U.S. Pat. Nos. 4,613,668 and 4,795,813 discuss the scarcity of thebaine and teach the total synthesis, or alternative synthesis, of the 14-hydroxymorphinans. Yet, the demand for thebaine remains.

A second reason for the limited availability of thebaine, and its high cost, is that the primary source of thebaine is extraction from the poppy plant, Papaver somniferum. Morphine is the major alkaloid that accumulates in capsules of Papaver somniferum. Thus, the supply of thebaine is to a great degree limited to some fraction of the demand for morphine.

Further synthetic routes to the preparation of the 14-hydroxymorphinans are known using the alkaloid, oripavine, as a starting material.

Oripavine

Oripavine has not been used as a starting material for the 14-hydroxymorphinans in any practical sense because it is not recoverable from Papaver somniferum in any practical yield. Thus, there is now no real shortage of this material, but only because there has never developed any demand for it.

A synthesis using oripavine to produce the ring-C bridged opiate, buprenorphine, is shown in Scheme A3.

Flow Scheme A3

-continued

X = protecting group buprenorphine naltrexone

X = protecting group

As compared to the synthesis from thebaine, this synthesis has an additional step. However, the protecting group, X, can be chosen from groups, such as, acetyl, benzoyl or trialkyl silyl so that the removal of X in the last step can be a high yielding and fast reaction as compared to the demethylation required with the use of thebaine.

Another synthesis using oripavine to produce the 14-hydroxymorphinan, naltrexone as representative of the nal-compounds, is shown in Scheme A4.

Flow Scheme A4 oripavine

As compared to the synthesis from thebaine, this synthesis has an additional step. However, as above, the protecting group, X, can be chosen from groups, such as, acetyl, benzoyl or trialkyl silyl so that the removal of X in the last step can be a high yielding and fast reaction as compared to the demethylation required with the use of thebaine.

Alkaloids are extracted from the poppy capsules of Papaver somniferum by two commercial methods. In one method, the immature capsule is cut and the latex collected from the wound. The air dried latex is opium which, according to the Merck Index, 11th edition, contains alkaloids in the amounts shown in Table I. In a second method, the mature poppy capsules and the poppy capsule stems are collected, and threshed to remove the seeds and form a straw. When necessary, the straw is dried to a water content below 16%. Solvent or water extraction is employed to remove the alkaloids from the straw. For the varieties of Papaver somniferum normally grown by the Applicants herein, the straw, on a dry basis, contains alkaloids in the amounts shown in Table I.

TABLE I

|  | opium | straw |
|---|---|---|
| morphine, % | 10–16 | 1–3 |
| codeine, % | 0.8–2.5 | 0.05–0.3 |
| oripavine, % | 0–0.1 | 0–0.05 |
| thebaine, % | 0.5–2 | 0.15–0.65 |

As can be seen, the yield of thebaine and oripavine is confounded with that of other alkaloids.

Where solvent or water or super critical fluid, such as $CO_2$, extraction is employed to remove the alkaloids from the straw, such method, as practised, involves the production of "Concentrate of Poppy Straw". Concentrate of Poppy Straw is defined as "The material arising when poppy straw has entered into a process for the concentration of its alkaloids, when such material is made available in trade," (MULTILINGUAL DICTIONARY OF NARCOTIC DRUGS AND PSYCHOTROPIC SUBSTANCES UNDER INTERNATIONAL CONTROL, United Nations, New York, 1983). Not inconsistent with the foregoing defininition, Concentrate of Poppy Straw is defined as "the crude extract of poppy straw in either liquid, solid or powder form which contains the phenanthrene alkaloids of the opium poppy," 45 U.S. Federal Register 77466, Nov. 24, 1980. When in liquid form, the liquid is preferably concentrated before entering into commerce. The generally preferred Concentrate of Poppy Straw is the powder form which results from simply removing the solvent or water following extraction of the poppy straw. In a more narrow sense, Concentrate of Poppy Straw should contain the alkaloids of Papaver somniferum in substantially their raw proportions. However, more broadly, certain of the alkaloids, or portions thereof, may be deleted from the Concentrate of Poppy Straw so long as at least two of the alkaloid components remain in their raw proportions, one to the other.

It is the object of the present invention to produce poppy straw of Papaver somniferum containing increased yields of thebaine and/or oripavine. It is another object of the present invention to produce such poppy straw containing little or no codeine or morphine.

It is an object of the present invention to produce opium of Papaver somniferum having increased yields of thebaine and/or oripavine. It is another object of the present invention to produce such opium having little or no codeine or morphine.

It is an object of the present invention to produce concentrate of poppy straw of Papaver somniferum having increased yields of thebaine and/or oripavine. It is another object of the present invention to produce such concentrate of poppy straw having little or no codeine or morphine.

It is yet another object of the present invention to provide for an improved process for the production of thebaine and/or oripavine. The improved process utilizes a mutagenized poppy plant of Papaver somniferum providing thebaine and/or oripavine in improved yield.

There is also provided by the present invention a method whereby the thebaine and/or oripavine yield of a poppy plant of Papaver somniferum may be improved.

Still another object of the present invention is to provide a poppy plant of Papaver somniferum having an improved yield of thebaine and/or oripavine with little or no morphine or codeine.

SUMMARY OF THE INVENTION

There is provided by the present invention an improved poppy straw of a stably reproducing Papaver somniferum for the extraction of thebaine and/or oripavine, the threshed straw having thebaine and oripavine constituting about 50% by weight or greater of the alkaloid combination consisting of morphine, codeine, thebaine and oripavine.

There is provided by the present invention an improved opium of a stably reproducing Papaver somniferum for the extraction of thebaine and/or oripavine, the opium having thebaine and oripavine constituting about 50% by weight or greater of the alkaloid combination consisting of morphine, codeine, thebaine and oripavine.

There is provided by the present invention an improved concentrate of poppy straw of a stably reproducing Papaver somniferum for the extraction of thebaine and/or oripavine, the concentrate of poppy straw having thebaine and oripavine constituting about 50% by weight or greater of the alkaloid combination consisting of morphine, codeine, thebaine and oripavine.

There is also provided by the present invention a method for the production of thebaine and/or oripavine which comprises the steps of:

a) harvesting poppy capsules of a stably reproducing Papaver somniferum to produce a straw where the plant is such a plant that the straw contains thebaine and oripavine constituting about 50% by weight or greater of the alkaloid combination consisting of morphine, codeine, thebaine and oripavine, and b) chemically extracting the thebaine and/or oripavine from the straw.

There is also provided by the present invention a method for the production of thebaine and/or oripavine which comprises the steps of:

a) collecting and drying the latex of the immature poppy capsules of a stably reproducing Papaver somniferum to produce opium where the plant is such a plant that the opium contains thebaine and oripavine constituting about 50% by weight or greater of the alkaloid combination consisting of morphine, codeine, thebaine and oripavine, and b) chemically extracting the thebaine and/or oripavine from the opium.

There is also provided by the present invention a method to improve the thebaine and/or oripavine yield of a stably reproducing Papaver somniferum, the method comprising the steps of:

a) exposing at least one poppy seed of Papaver somniferum to a mutagenizing agent, b) growing the at least one poppy seed to produce a plant bearing a leaf or an immature poppy capsule, optionally through multiple self-fertilized generations, c) sampling the leaf or poppy capsule for the presence of thebaine, oripavine, morphine and codeine, and d) repeating steps a) to c) until a poppy plant of Papaver somniferum is obtained having thebaine and oripavine constituting about 50% by weight or greater of the alkaloid combination consisting of morphine, codeine, thebaine and oripavine.

There is also provided by the present invention a stand of a stably reproducing Papaver somniferum, which upon the harvesting of their poppy capsules will yield a poppy straw having thebaine and oripavine constituting about 50% by weight or greater of the alkaloid combination consisting of morphine, codeine, thebaine and oripavine, each on a dry weight basis, or alternatively, which upon the collection and drying of the latex from their immature poppy capsules will yield an opium having thebaine and oripavine constituting about 50% by weight or greater of the alkaloid combination consisting of morphine, codeine, thebaine and oripavine.

There is also provided by the present invention a stand of a stably reproducing Papaver somniferum, in which the production or activity of codeinone reductase enzyme (NADPH) has been substantially inhibited with the result that upon the harvesting of their poppy capsules, the poppy plants will yield a poppy straw having thebaine and oripavine constituting about 50% by weight or greater of the alkaloid combination consisting of morphine, codeine, thebaine and oripavine, or alternatively, which upon the collection and drying of the latex from their immature poppy capsules will yield an opium having thebaine and oripavine constituting about 50% by weight or greater of the alkaloid combination consisting of morphine, codeine, thebaine and oripavine.

DETAILED DESCRIPTION OF THE INVENTION

Utilizing the mutagenized plants of Papaver somniferum as described herein, persons skilled in the art easily know how to grow them, reproduce them, collect the latex or the dried straw and purify the thebaine and/or oripavine. As one enablement of the present invention, seeds to the mutagenized plants of Papaver somniferum, as described herein, have been deposited under the Budapest Treaty with the American Type Culture Collection, 12301 Parklawn Drive, Rockville, Md. 20852, U. S. A., on Jul. 9, 1996, under Accession No. ATCC 97652, and will be made available upon the maturation of this application into a patent. The availability of these seeds if not to be construed as a license to practice this invention in contravention of rights granted under the authority of any government in accordance with its patent or breeder's rights laws. Regardless of the enablement provided by this deposit, persons skilled in the art of mutagenizing seed, can obtain the seed herein by employing the mutagenesis process as described below.

The production of mutagenized seed is well known in the art. Methods of seed mutagenesis as well as mutagens suitable for use in these methods, such as, ethyl methanesulfonate (EMS), are described in the Manual on Mutation Breeding, 2nd ed., I.A.E.A., Vienna 1977 or in Plant Breeding, Principles and Prospects, Chapman and Hall, London 1993. For X-ray mutagenized seeds, hydrated seeds might be treated with 20,000 rads, (30 cm from the source for 45 minutes using a filter). X-ray mutagenesis is described and compared to EMS mutagenesis by Filippetti, A. et al., "Improvement of Seed Yield in Vicia Faba L. By Using Experimental Mutagenesis II Comparison of Gamma-Radiation and Ethyl-Methane-Sulphonate (EMS) in Production of Morphological Mutants", Euphytica 35 (1986) 49–59. DEB, diepoxybutane, mutagenized seeds might be obtained by soaking the seeds in water overnight, then soaking in 22 mM DEB for 4 hours, followed by extensive washing. Further mutagens include ethyl-2-chloroethyl sulphide, 2-chloroethyl-dimethylamine, ethylene oxide, ethyleneimine, dimethyl sulphonate, diethyl sulphonate, propane sulphone, beta-propiolactone, diazomethane, N-methyl-N-nitrosourethane, acridine orange and sodium azide. Applicants employed and prefer EMS as the mutagen herein.

Mutagenesis utilizing EMS is well described in the literature. The Manual on Mutation Breeding, supra, reports a preferred EMS mutagenesis process for barley seeds as practiced by K. Mikaelson. In this preferred process, the seeds are prepared, pre-soaked, treated with the mutagen and post-washed.

In the preparation, uniform size seeds are selected and placed in mesh polyethylene bags, about 200 seeds. Subsequently, the seeds are kept in a dessiccator over a 60% glycerol solution, which gives the seeds a moisture content of about 13%. In pre-soak, the seed bags are transferred to beakers with distilled or deionized water and soaked for 16–20 hours at a temperature of 20–22° C. The pre-soak period is important to the uptake or diffusion of mutagen. The pre-soak should be sufficient to promote diffusion of the mutagen into the seed and at the same time stimulate the embryo meristem tissue to start DNA synthesis. It is at this point that high mutation frequency can be achieved with minimal chromosome damage. To treat with the mutagen, the seed bags are transferred to beakers containing a solution of EMS in distilled or deionized water. For barley and wheat, the maximal mutation frequencies are obtained under treatment conditions where the EMS concentration is 0.05–0.1 M, the bath temperature is 30–35° C., and the exposure time of the seeds to the bath is 0.5–2 hours. Relatively weak treatments are preferred in mass screening to achieve maximal mutation with minimal physiological damage. Such treatments give better germinability and survival, less plant growth reduction and less sterility compared with stronger treatments. A thorough post-wash in water after the EMS treatment is essential. This post-wash can be carried out in running tap water, preferably at not less that 15° C., for a period of not less than 4 hours. The EMS should be removed by the post-wash in order to prevent uncontrollable aftereffects by the mutagen. After post-washing, the seeds should be planted as soon as possible. If the seeds cannot be planted soon after the mutagenesis process, they should be immediately dried back to a moisture content of about 13%. This can be accomplished by simply air drying the seeds at room temperature and a reasonably low relative humidity.

Persons skilled in the art will recognize that this preferred mutagenesis method for barley and wheat seeds can be easily modified for poppy seeds. In the case of poppy seeds, it has been found useful and convenient by the inventors hereof to dispense with dessication, to extend the time of pre-soak to up to 48 hours and to lower the bath temperature of mutagen treatment to room temperature. Other modifications will be apparent to skilled practitioners.

After the seeds have been exposed to the mutagen, the seeds are grown to maturity in controlled conditions and self-pollinated. The seeds from the mature plant are taken and at least one seed is planted to grow an $M_2$ generation. The $M_2$ generation is screened for alkaloid production. Of course, it is possible to screen the $M_1$ generation, but there are several advantages to screening the $M_2$ generation. Firstly, screening the $M_2$ generation insures that the trait resulting from mutagenesis can be inherited.

Secondly, by growing the $M_2$ generation, the basic hardiness of the plant is proven before screening. Thirdly, traits resulting from mutagenesis are generally inherited as recessive genes, and these will be homozygous in the $M_2$ generation, i.e., they will not be masked by a dominant gene. The $M_2$ plants can be grown to produce an immature capsule, but it is possible to save time and labor if the plant is screened at an earlier stage of growth. It is recommended that the plants be screened at a point beginning at the 10 leaf stage, up to the "running-up" stage, where the plant reaches about 6 inches in height. The screening process itself is the most labor intensive. Thus, to improve return on labor, only plants that appear healthy should be screened.

In the screening process, the objective is to measure each plant for morphine, codeine, thebaine and oripavine content. This can be accomplished by extracting, for example, a dry leaf into a liquid buffer or by dissolving a latex sample into a buffer. The buffer solutions are placed onto 96 well trays and fed mechanically through any of the high-throughput HPLCs available on the market.

Plants of with interesting alkaloid contents are grown further and examined in more detail. According to procedure herein, a second sample is taken from about 1/20 plants to clarify the results of the initial screen, A plant having high thebaine and oripavine and substantially no morphine or codeine was found after screening approximately 8,000 plants.

As stated above, there is obtained by the present invention, a threshed poppy straw or opium having thebaine and oripavine constituting about 50% by weight or greater of the alkaloid combination consisting of morphine, codeine, thebaine and oripavine. Preferably, thebaine and oripavine constitute 80% by weight or greater of the alkaloid combination. More preferably, thebaine and oripavine constitute 95% by weight or greater of the alkaloid combination. Most preferably, there is substantially no morphine or codeine in the alkaloid combination.

The desired traits, i.e. high thebaine and oripavine content versus morphine or codeine content, once established are highly heritable. To maintain the desired traits, care should be taken to prevent cross-pollination with normal plants unless such cross-pollination is part of a controlled breeding program.

The theory whereby mutagenesis has been found to be capable of raising the thebaine and/or oripavine content of Papaver somniferum relative to the morphine and codeine content is not capable of a certain or definite explanation at this time. The mutagenesis may have resulted in the enhancement of certain enzyme activity in a qualitative or quantitative manner converting, for example, morphine to morphinone. Alternatively, the mutagenesis might have modified the biosynthesis pathway in any number of ways to minimize the production of morphine and codeine. Despite the fact that definite answers are not now available, there are good reasons to believe that the correct answer is known.

Papaver somniferum is postulated to have two biosynthetic pathways from thebaine to morphine as shown in Flow Scheme B. Pathway A via neopinone, codeinone and codeine was proposed by Parker, H. I., J. Am. Chem. Soc., 94, 1276–1282 (1972). Pathway B via oripavine and morphinone was proposed by Brochmann-Hanssen, E., Planta Med., 50, 343–345 (1984). Codeinone and morphinone vary only in the presence of a methyl group at the 3-position of codeinone. The enzyme codeinone reductase (NADPH) is believed to be active in both pathways, reducing codeinone to codeine and morphinone to morphine. Codeinone reductase has been isolated, its activity is described and its physical properties are characterized by Lenz, R., and Zenk, M. H., Eur. J. Biochem, 233, 1, 132–139 (1995).

By the methods herein, a variety of Papaver somniferum was obtained having substantially no morphine or codeine. Both Pathway A and Pathway B were made inoperative to produce morphine. It is highly unlikely that the production or activity of two different enzymes, one active in each pathway, was simultaneously inhibited in a given mutagenized plant. It is far more likely that the production or activity of a single enzyme was inhibited that is active in both pathways. Codeinone reductase is the only known enzyme active in both pathways. Thus, it is believed, for the Papaver somniferum variety described herein, that the production or activity of codeinone reductase (NADPH) has been substantially inhibited. Stably reproducing Papaver somniferum in accordance with the present invention may also be obtained by recombinant DNA techniques. In particular, after isolation and sequencing of the gene coding for codeinone reductase, the gene may be modified or deleted to inhibit or prevent the production of codeinone reductase. Techniques for modifying or deleting specific regions of DNA sequences are well known to those skilled in the art.

Flow Scheme B

Recovering thebaine and/or oripavine from either the dried straw or from the opium of Papaver somniferum is a process well established in the art. Until now, thebaine has been extracted from this plant as a part of the process of extracting morphine and codeine. In one process, the straw is treated with a small amount of lime and water to soften the capsules and to form a free base of the alkaloids. Countercurrent extraction of the softened straw with methanol, ethanol or other suitable solvent forms a solvent/water extract or "miscella" containing the alkaloids, with morphine at a concentration of about 1 g/L where the straw is from standard Papaver somniferum. The volume of the miscella is reduced about 30× under vacuum to produce an aqueous concentrate. Thebaine is extracted from aqueous concentrate using a liquid/liquid extraction with toluene, adjusting pH for the best separation of thebaine. The thebaine is recovered from the toluene. Of course, recovering thebaine from the improved Papaver somniferum provided herein will be facilitated by the fact that the concentration of the thebaine in the miscella will be much higher than that of other alkaloids and thus can be more easily collected by precipitation. Also, in the substantial absence of morphine and codeine, the thebaine might be directly extracted from the straw using toluene. In the case of oripavine, it has not been separately recovered on a commercial scale, however, oripavine may be recovered from an aqueous concentrate by adjusting to basic pH and extracting with organic solvent such as toluene. The oripavine will remain in the aqueous layer and the thebaine will be found in the organic solvent. The oripavine can then be recovered from the aqueous phase by adjusting the pH to precipitate the oripavine.

The following examples are presented as specific illustrations of the claimed invention. It should be understood, however, that the invention is not limited to the specific details set forth in the Examples.

EXAMPLES

Seeds of Papaver somniferum were obtained of about uniform size, dried to about 8% LOD (loss on drying) and placed in a mesh polyethylene bag at a weight of about 5 grams or about 12,500 per bag. The seeds were pre-soaked in beakers of distilled water containing 4 mM $CaSO_4$ at room temperature for about 36 hours. Immediately after pre-soak, the seed bags were immersed in a mutagen bath containing either 0.3% v/v (~0.028 M) or 0.5% v/v (~0.047 M) ethyl methanesulphonate (EMS) at room temperature for thirty minutes. Immediately following the mutagen bath, the seed bags were post-washed in running tap water for a period of four hours. Following post-wash, the seeds were kept moist and planted within one hour.

The seeds were planted in outdoor plots and grown to maturity. The planting technique employed was in all respects normal for poppy trial work, and similar to commercial poppy growing. The seeds were sown using a "cone seeder" or trial plot drill. Seed depth was about 1 cm. Fertiliser containing N, P and K was used. The plots were irrigated immediately after sowing. The poppy flowers were self-pollinated and the majority of the flowers were covered with paper bags of bleached white "kraft" paper to prevent cross pollination. Seeds were harvested from those plants which grew vigorously and appeared healthy. Only a very few were pale and grew poorly. A second, $M_2$, generation was grown from the harvested seeds. These seeds were planted in trays containing 200 plants. The last row of each tray was reserved for a known high thebaine variety of poppy to serve as a control. When the $M_2$ plants were between the 10 leaf stage and the "running-up" stage, about 6 inches high, they were screened for alkaloid content.

The screening process was basically a three step process. In the first step, a leaf was cut from an $M_2$ plant and about 0.5 μL of latex was collected at the wound. The latex was diluted in a microcentrifuge tube with 250 μL of buffer. The buffer contained 0.2 M ammonium phosphate, 20% ethanol, and had a pH of 4.5. The microcentrifuge tube was briefly held to a vortex shaker to insure mixing. In the second step, the buffered solution was centrifuged to substantially eliminate suspended solids and about 200 μL was decanted into a 40 mm×8 mm autoanalyser tube. Additional buffer, 250

μL, was added to each auto analyser tube so that the sampling needle of the autoanalyser could reach the solution. In the third step, the autoanalyser tubes were loaded into a 96 tube carousel with a standard sample containing morphine, codeine, thebaine, and papaverine and the carousel was inserted into the auto injector module of a Waters HPLC system. The HPLC mobile phase was aqueous methanol (approximately 30%) containing ammonium acetate buffer (0.08–0.12 M), pH 4–5. The flow rate of the mobile phase was 0.8–1.5 mL/minute. A Whatman Partisphere SCX column (4.6×125 mm) was used at a temperature of 40° C. A Waters 440 UV detector was used to detect the peaks at 254 nm. The data was interpreted and collated on a Waters Millennium Data Station. The system was used to analyse for morphine, codeine, oripavine, thebaine and papaverine.

There were typically screened about 900 plants per week. Of these, about 50 were retested to confirm the alkaloid profiles. Out of about 1,8000 plants screened, 365 were repotted and grown to maturity as being of further interest.

Plant D233, an $M_2$ generation plant designated "Norman", was first tested and showed no chromatogram peak for morphine, the only plant found with zero morphine. Eight days after the initial sample, a retesting using the same procedure, but with a gradient HPLC system, showed a very small morphine peak. Norman was repotted along with a high thebaine variety of poppy, a control plant as described above, at the same stage of development and both plants were allowed to produce an immature capsule. A latex sample was collected from the capsule of both plants and tested with a gradient HPLC. Four weeks after the initial sample, a retesting of Norman using the same procedure, but again with a gradient HPLC system, showed no morphine and no codeine. Norman was self fertilised by covering the flowers with a piece of tissue paper fastened with a plastic coated wire. The capsules of Norman and the control plant were harvested at maturity, about 8 to 9 weeks after the intial sample was taken. Norman produced 3 capsules providing, fresh weight, about 2.4 g of straw (the threshed capsule material) and about 3.5 g of seed. The straw of both Norman and the control plant were extracted using a lime extraction for morphine and an acid extraction for thebaine, codeine and oripavine. The lime extraction, the acid extraction and the analysis procedure are described below under the heading "Alkaloid Extraction Procedure". Analysis of the extractant, assuming a water content of about 5% in the dry straw, is reported in Table II, where the reported figure is percent by weight of the dry straw.

TABLE II

|  | NORMAN ($M_2$) | CONTROL | TYPICAL CROP |
|---|---|---|---|
| morphine, % | nil | 1.79 | 1.44* |
| codeine, % | nil | 0.37 | 0.10* |
| oripavine, % | 0.43 | 0.02 | 0.03* |
| thebaine, % | 1.60 | 0.26 | 0.15* |
| Total, % | 2.03 | 2.44 | 1.72* |

The figures of Table II are the average of two samples, with the exeption of those marked with the asterisk (*), which are gross estimates. The reported "Typical Crop" figure is a sample from the 1995 Tasmanian harvest.

Using the seeds obtained from Norman, as described above, an $M_3$ generation Norman was planted, self fertilised, harvested and tested along with a high thebaine variety control plant as also described. Analysis of the extractant, assuming a water content of about 5% in the dry straw, is reported in Table III, where the reported figure is percent by weight of the dry straw.

TABLE III

|  | NORMAN ($M_3$) | CONTROL |
|---|---|---|
| morphine, % | nil | 2.23 |
| codeine, % | 0.05 | 0.41 |
| oripavine, % | 0.74 | 0.07 |
| thebaine, % | 1.68 | 0.30 |
| Total, % | 2.47 | 3.01 |

The figures of Table IIII are the average of two samples.

Alkaloid Extraction Procedure

All samples were run on an HPLC Gradient System having an Alltech Altima C18 5 micron column, 4.6×250 mm, with a 5 microliter injection volume, operating at 284 nm and at a temperature of 40° C. For all calculations:

Asa=Area of Sample

C=Concentration of Standard

Ast=Area of Standard

LOD=Loss on drying

1. Acid Extraction (for Thebaine, Codeine, Oripavine Analysis)

In the acid extraction, 0.100 g of ground capsule was mixed with 5 ml of a solution of 10% acetic acid, 10% water and 80% methanol. This was agitated for 20 minutes, and then filtered. The filtrate was directly injected into the HPLC.

Calculation:

% Alkaloid (dry basis)=assayed wt alkaloid/dry wt of sample*100

Assayed wt Alkaloid=Asa/Ast*C*((5+LOD*0.1/100)/1000)

Assuming 5% LOD, this becomes=Asa/Ast*C*0.005005

Wt of Sample=0.100((100−LOD)/100)

Assuming 5% LOD, this becomes=0.095

Thus,

%Alkaloid(DWB)=(Asa/Ast*C*0.005005)/0.095*100= Asa/Ast*C*5.268

2. Lime Extraction (for Morphine Analysis)

In the lime extraction, 0.100g of ground capsule was mixed with 0.020 g of lime and 10 ml of water. This was agitated for 20 minutes, and 20 then filtered. 4 ml of filtrate is transferred to a 5 ml volumetric flask and made up to volume with 20% oxalic acid solution. This was then filtered and the filtrate injected directly into the HPLC.

Calculation:

% Alkaloid (dry basis)=assayed wt alkaloid/dry wt of sample*100

Assayed wt Alkaloid=Asa/Ast*C*5/4((10+LOD*0.1/100)/1000)

Assuming 5% LOD, this becomes=Asa/Ast*C*0.0125

Wt of Sample=0.100((100−LOD)/100)

Assuming 5% LOD, this becomes=0.095

Thus,

%Alkaloid(DWB)=(Asa/Ast*C*0.0125)/0.095*100= Asa/Ast*C*13.157

What is claimed is:

1. A method for the production of thebaine and/or oripavine which comprises the steps of:

a) harvesting poppy capsules of a stably reproducing Papaver somniferum to produce a straw where the plant is such a plant that the straw contains thebaine and oripavine constituting about 50% by weight or greater of the alkaloid combination consisting of morphine, codeine, thebaine and oripavine, and b) chemically extracting the thebaine and/or oripavine from the straw.

2. The method of claim 1 wherein thebaine and oripavine constitute 80% by weight or greater of the alkaloid combination.

3. The method of claim 1 wherein thebaine and oripavine constitute 95% by weight or greater of the alkaloid combination.

4. The method of claim 1 wherein there is substantially no morphine or codeine in the alkaloid combination.

5. A method for the production of thebaine and/or oripavine which comprises the steps of:

a) collecting and drying the latex of the immature poppy capsules of a stably reproducing Papaver somniferum to produce opium where the plant is such a plant that the opium contains thebaine and oripavine constituting about 50% by weight or greater of the alkaloid combination consisting of morphine, codeine, thebaine and oripavine, and b) chemically extracting the thebaine and/or oripavine from the opium.

6. The method of claim 5 wherein thebaine and oripavine constitute 80% by weight or greater of the alkaloid combination.

7. The method of claim 5 wherein thebaine and oripavine constitute 95% by weight or greater of the alkaloid combination.

8. The method of claim 5 wherein there is substantially no morphine or codeine in the alkaloid combination.

9. A method for the production of a pharmaceutically useful 14-hydroxymorphinan, said method comprising producing thebaine and/or oripavine by the method of claim 1, and chemically converting said thebaine and/or oripavine to the desired 14-hydroxymorphinan.

10. A method according to claim 9, wherein said 14-hydroxymorphinan is selected from the group consisting of oxycodone, naloxone, naltrexone, nalbuphine, nalmefene and buprenorphine.

* * * * *